(12) United States Patent
Redl et al.

(10) Patent No.: US 8,469,289 B2
(45) Date of Patent: *Jun. 25, 2013

(54) TISSUE SEALANT APPLICATOR SYSTEM

(75) Inventors: Heinz Redl, Vienna (AT); Zafar Khakpour, Vienna (AT); Scott R. Ariagno, Lemont, IL (US); Andreas Kellner, Vienna (AT); Lillian G. Zakarija, Chicago, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 25 days.

This patent is subject to a terminal disclaimer.

(21) Appl. No.: 13/053,201

(22) Filed: Mar. 21, 2011

(65) Prior Publication Data

US 2011/0172703 A1 Jul. 14, 2011

Related U.S. Application Data

(63) Continuation of application No. 12/390,014, filed on Feb. 20, 2009, now Pat. No. 7,909,267, which is a continuation of application No. 11/331,243, filed on Jan. 12, 2006, now Pat. No. 7,537,174.

(60) Provisional application No. 60/643,368, filed on Jan. 12, 2005.

(51) Int. Cl.
*A62C 13/62* (2006.01)
*A62C 5/00* (2006.01)
*B05B 9/04* (2006.01)
*B05B 11/02* (2006.01)
*F23D 11/10* (2006.01)

(52) U.S. Cl.
USPC ........... 239/321; 239/306; 239/311; 239/418; 222/137; 222/391

(58) Field of Classification Search
USPC ................. 239/302, 303, 304, 306, 310, 311, 239/320, 321, 322, 372, 418, 419.3; 222/137, 222/145.5, 327, 391; 604/82, 191, 289
See application file for complete search history.

(56) References Cited

U.S. PATENT DOCUMENTS

4,846,405 A * 7/1989 Zimmermann ............... 239/422
5,582,596 A * 12/1996 Fukunaga et al. ............ 604/191

(Continued)

FOREIGN PATENT DOCUMENTS

EP 0634140 1/1995
EP 1078600 2/2001

(Continued)

OTHER PUBLICATIONS

International Search Report for International Application No. PCT/US2006/000970 (Jun. 27, 2006.

(Continued)

*Primary Examiner* — Ryan Reis
(74) *Attorney, Agent, or Firm* — Marshall, Gerstein & Borun LLP

(57) ABSTRACT

A tissue sealant applicator system includes a tissue sealant applicator having an elongate body forming a bore containing a tissue sealant component, a piston, and a spray adaptor in fluid communication with the bore and forming a gas flow path. The system also includes a control unit adapted to be connected to a gas source, and a first gas passageway connecting the gas flow path and the control unit. The applicator includes an actuating member cooperatively associated with the piston to eject the tissue sealant from the bore upon user actuation. The control unit is adapted to supply gas from the gas source to the first gas passageway essentially simultaneously with user actuation of the actuating member, and to permit the supply of gas to the spray adaptor from the gas source to continue to flow for a predetermined time delay after the user stops actuating the actuating member.

23 Claims, 11 Drawing Sheets

U.S. PATENT DOCUMENTS

| | | | |
|---|---|---|---|
| 5,605,541 | A | 2/1997 | Holm |
| 5,665,067 | A * | 9/1997 | Linder et al. .................... 604/82 |
| 5,759,169 | A | 6/1998 | Marx |
| 5,759,171 | A | 6/1998 | Coelho et al. |
| 5,887,755 | A | 3/1999 | Hood, III |
| 5,944,709 | A | 8/1999 | Barney et al. |
| 5,971,956 | A | 10/1999 | Epstein |
| 6,007,515 | A | 12/1999 | Epstein et al. |
| 6,047,861 | A | 4/2000 | Vidal et al. |
| 6,059,749 | A | 5/2000 | Marx |
| 6,206,905 | B1 | 3/2001 | Holm et al. |
| 6,331,172 | B1 | 12/2001 | Epstein et al. |
| 6,432,084 | B1 | 8/2002 | Levinson et al. |
| 6,454,786 | B1 | 9/2002 | Holm et al. |
| 6,461,325 | B1 | 10/2002 | Delmotte et al. |
| 6,461,361 | B1 | 10/2002 | Epstein |
| 6,464,663 | B1 * | 10/2002 | Zinger ............................ 604/82 |
| 6,471,667 | B1 | 10/2002 | Epstein |
| 6,540,716 | B1 | 4/2003 | Holm |
| 6,565,539 | B1 * | 5/2003 | Zinger et al. ................. 604/191 |
| 6,585,696 | B2 | 7/2003 | Petersen et al. |
| 6,613,020 | B1 * | 9/2003 | Holm et al. .................. 604/191 |
| 6,733,472 | B1 | 5/2004 | Epstein et al. |
| 6,770,050 | B2 | 8/2004 | Epstein |
| 6,852,099 | B2 | 2/2005 | Redl et al. |
| 6,860,870 | B2 | 3/2005 | Pichon et al. |
| 6,874,657 | B2 | 4/2005 | Metzner et al. |
| 6,884,230 | B1 | 4/2005 | Epstein et al. |
| 7,537,174 | B2 | 5/2009 | Redl et al. |
| 7,909,267 | B2 * | 3/2011 | Redl et al. ..................... 239/321 |

FOREIGN PATENT DOCUMENTS

| | | |
|---|---|---|
| GB | 962163 | 7/1964 |
| JP | 7255729 | 10/1995 |
| JP | 2001-515401 | 9/2001 |
| RU | 2195897 | 1/2003 |
| RU | 2196536 | 1/2003 |
| SU | 1666571 | 7/1991 |
| SU | 1526275 | 6/1999 |
| WO | WO 95/31138 | 11/1995 |
| WO | WO 96/39212 | 12/1996 |
| WO | WO 97/20585 | 6/1997 |
| WO | WO 03/068296 | 8/2003 |

OTHER PUBLICATIONS

Extended European Search Report for corresponding European patent application No. EP12177176.0, dated Sep. 4, 2012.

* cited by examiner

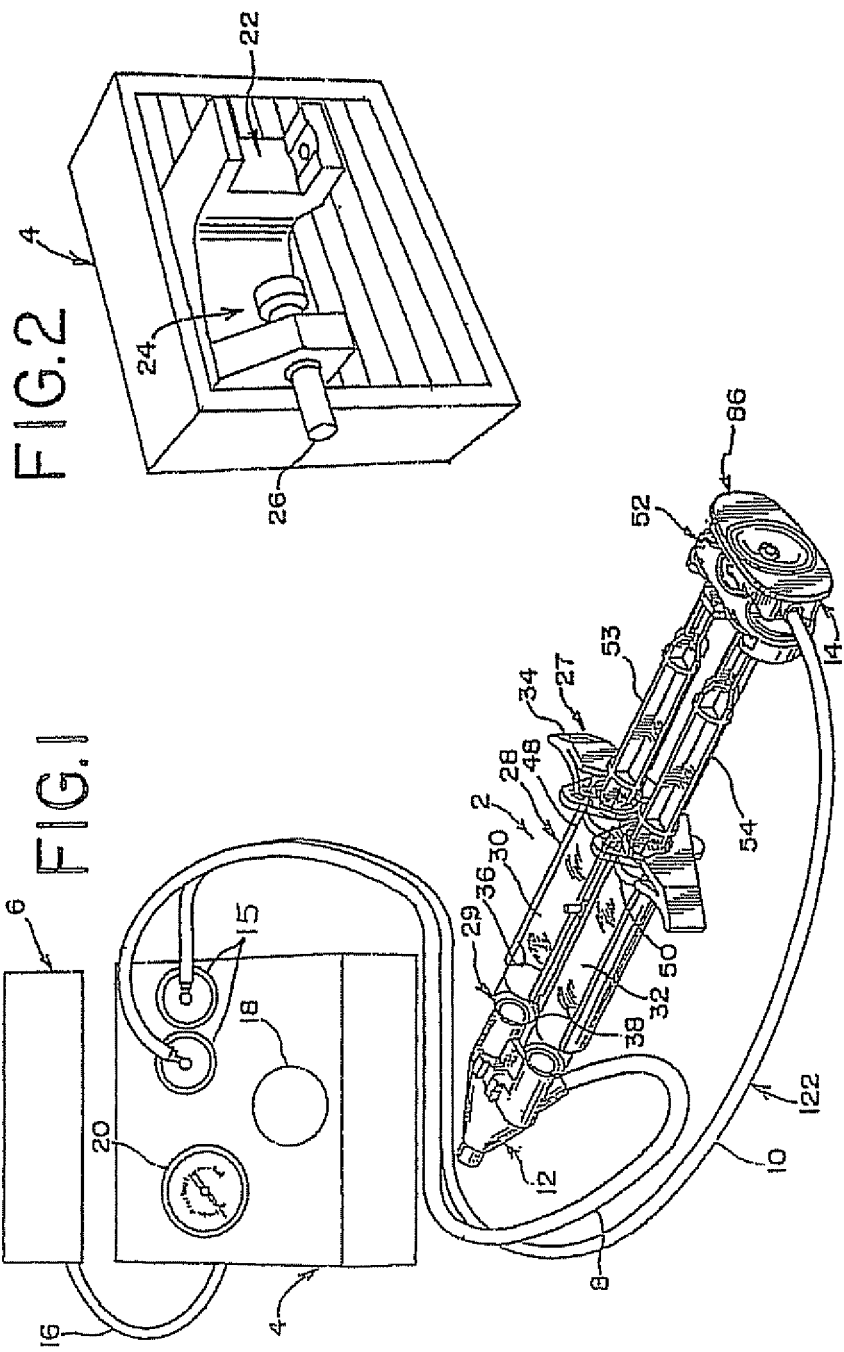

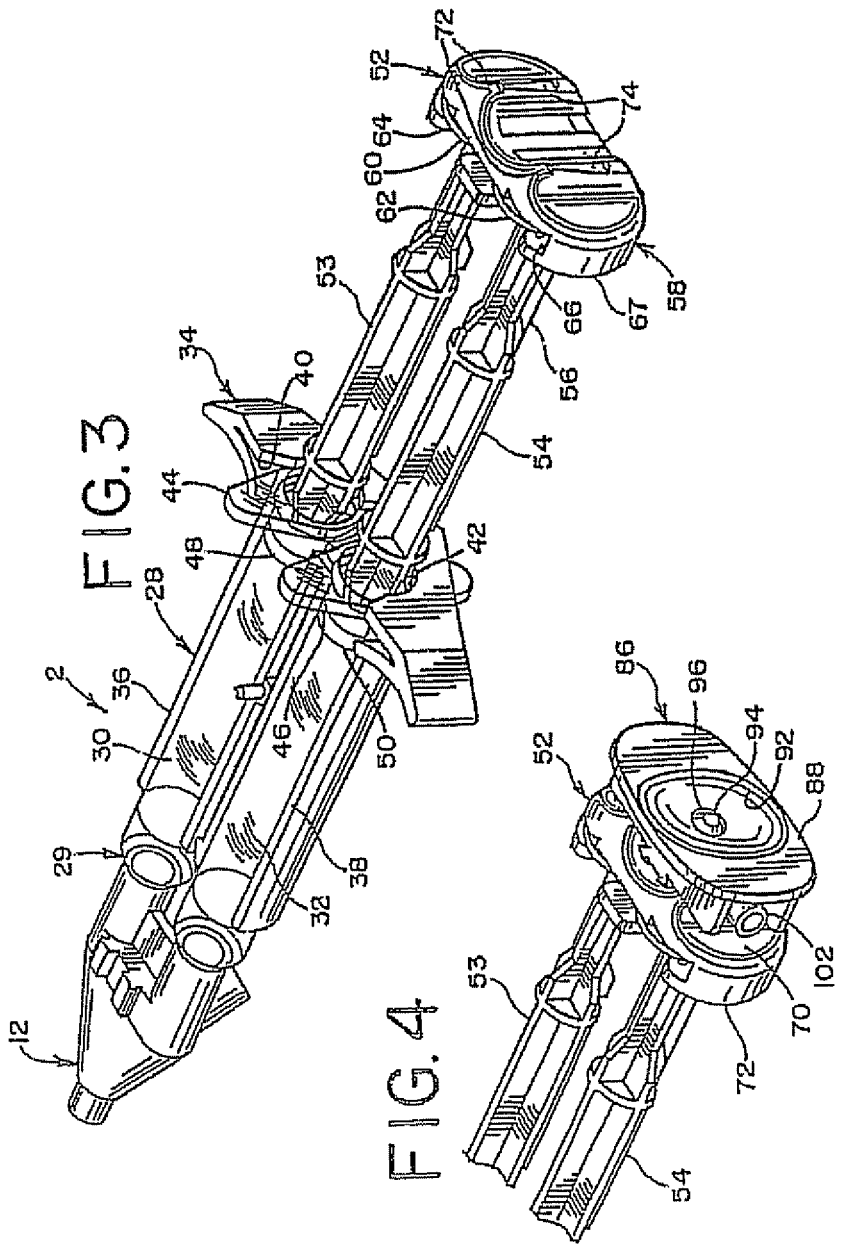

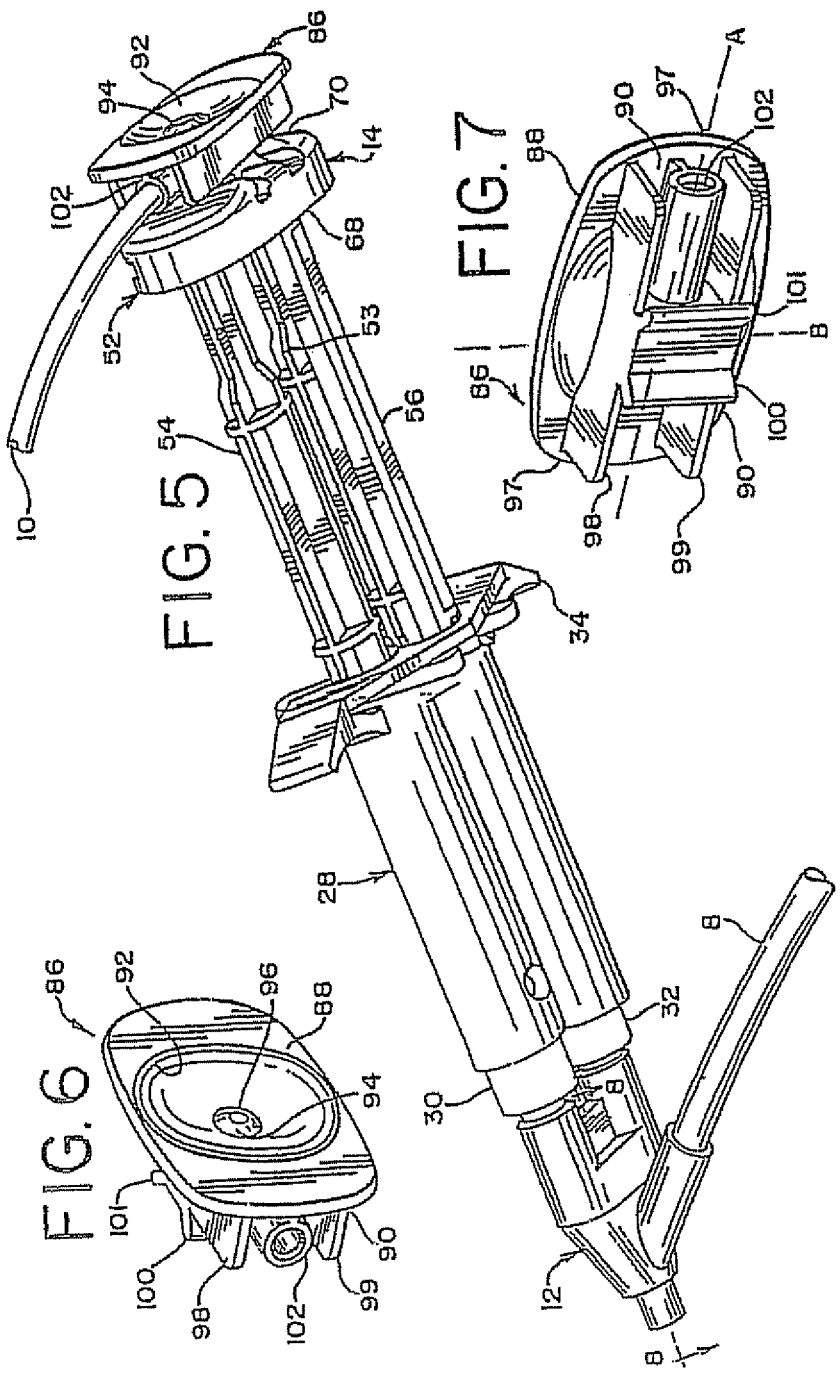

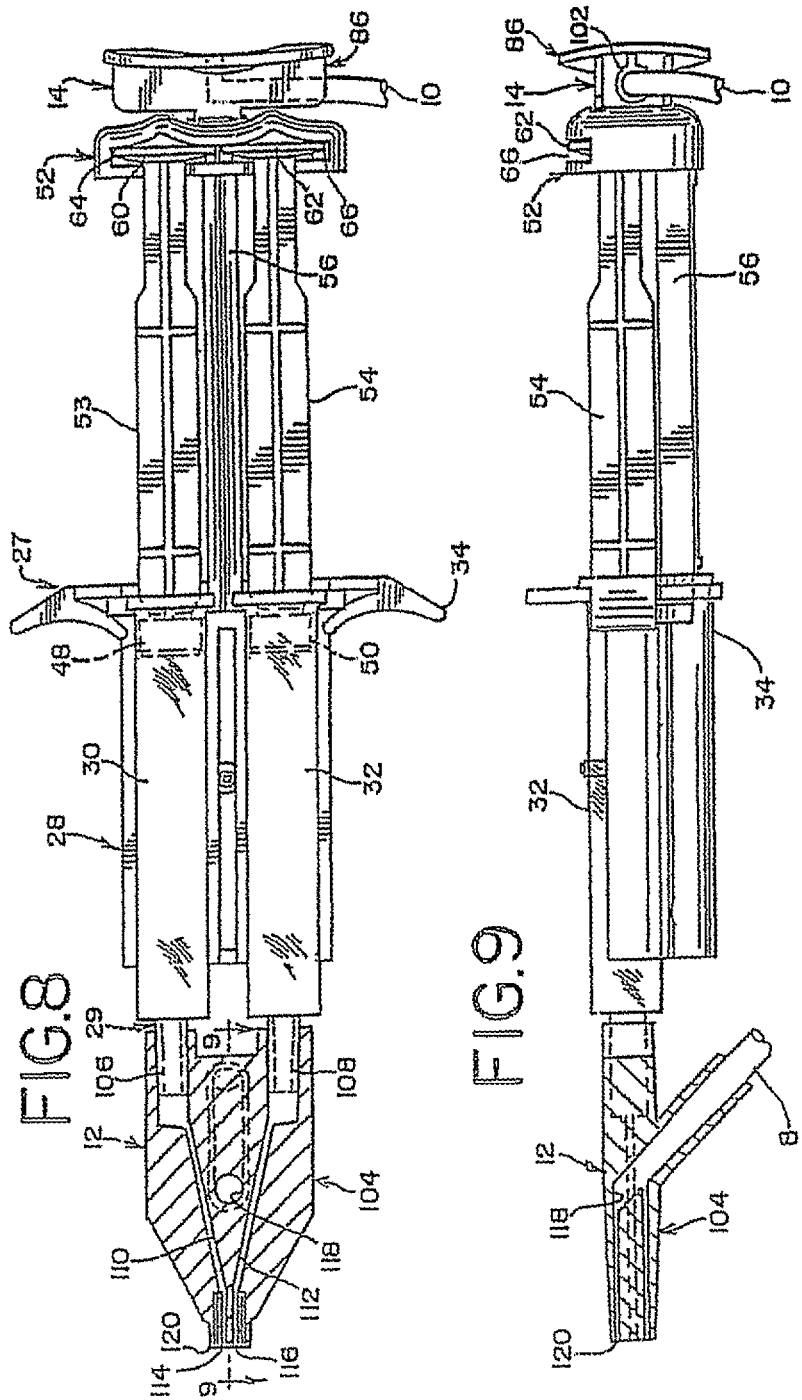

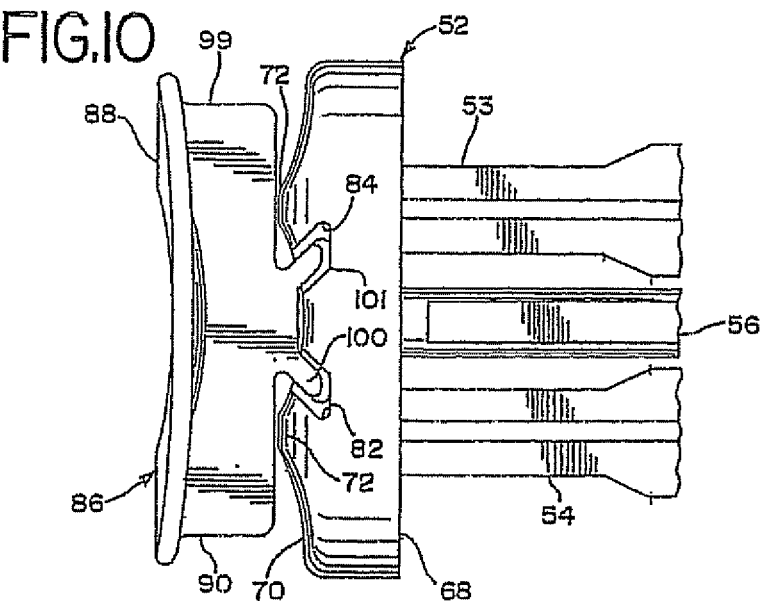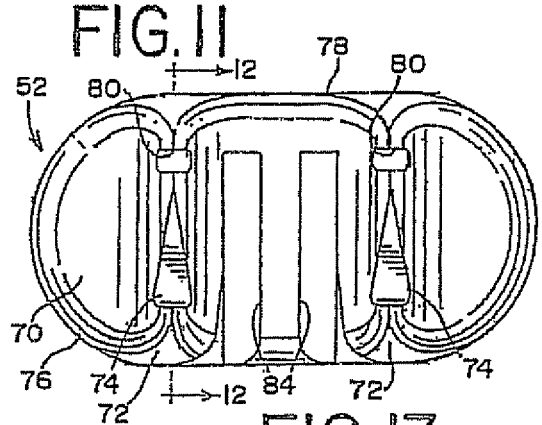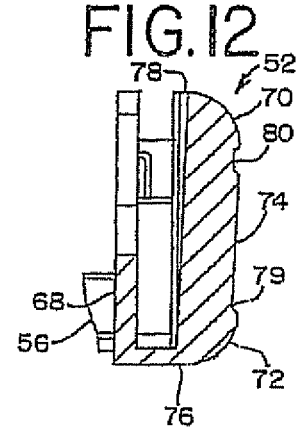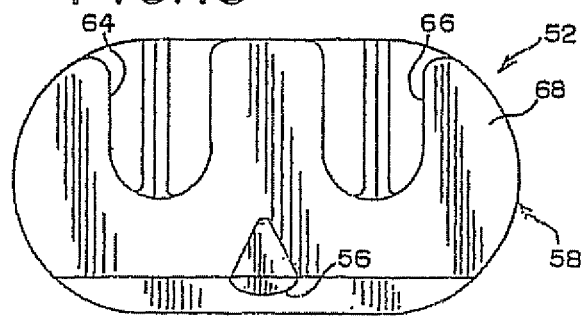

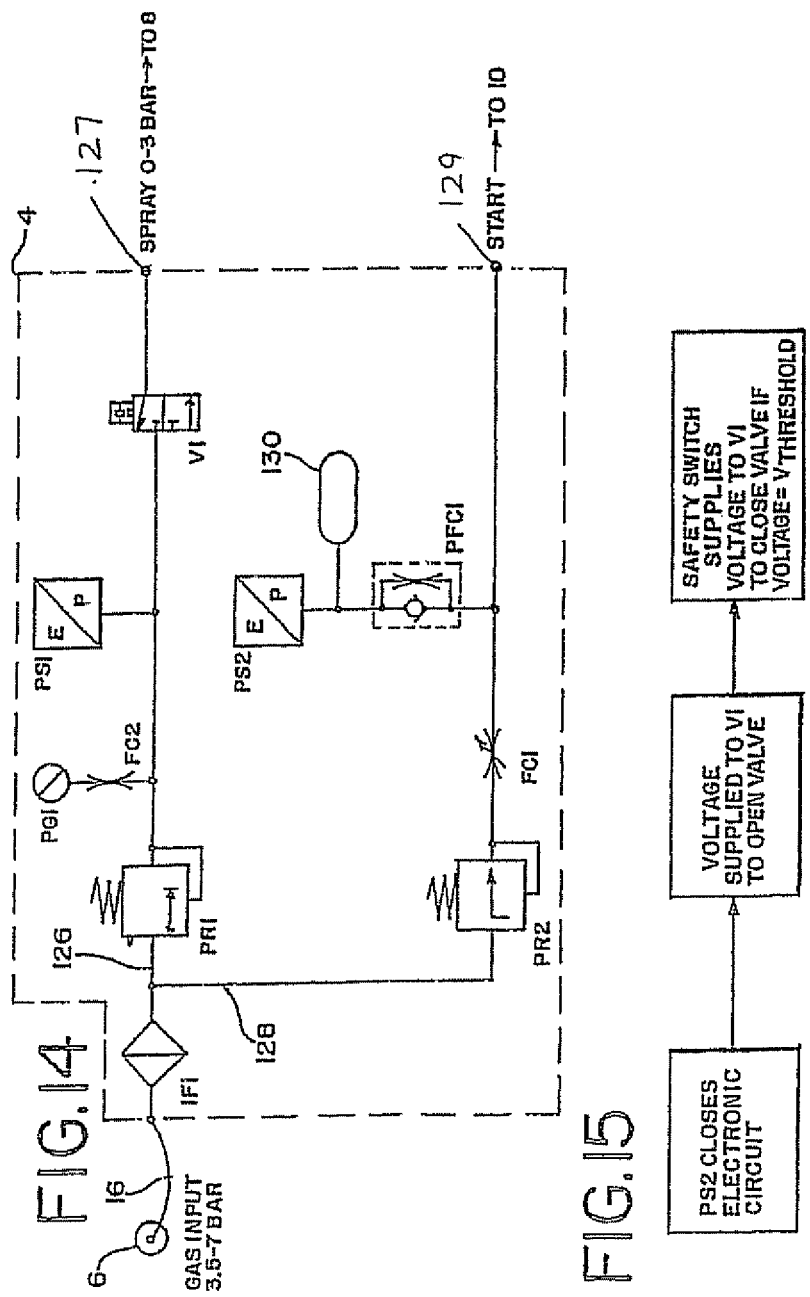

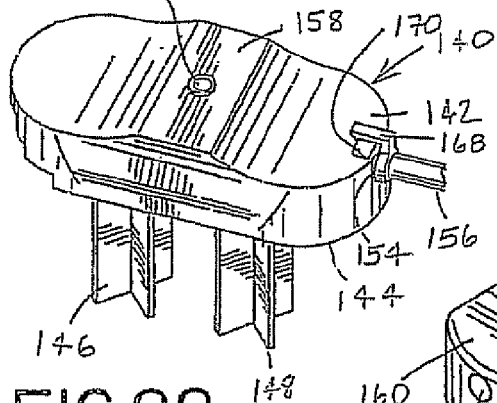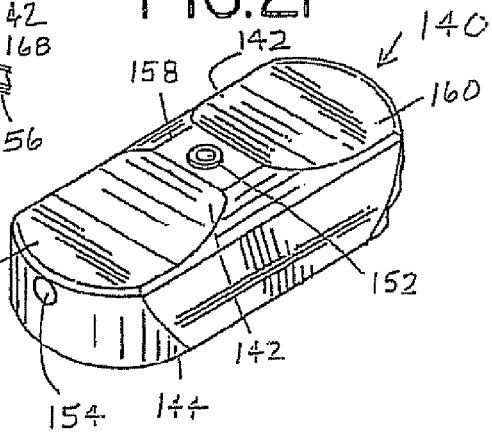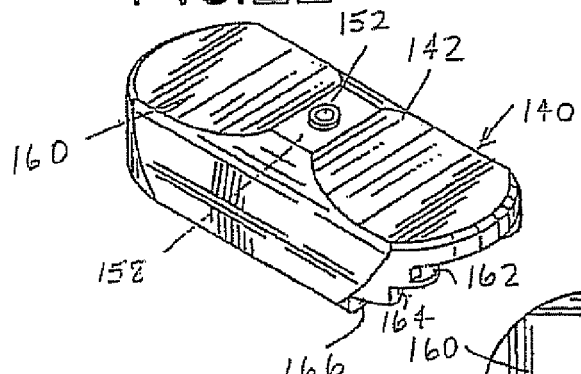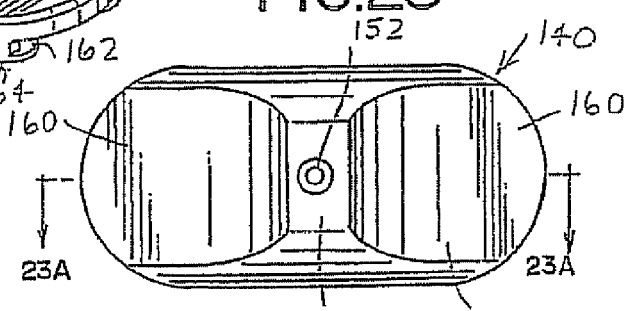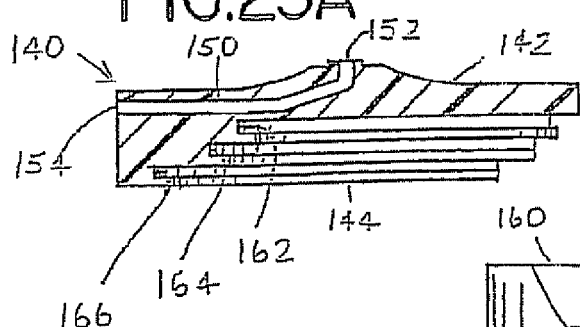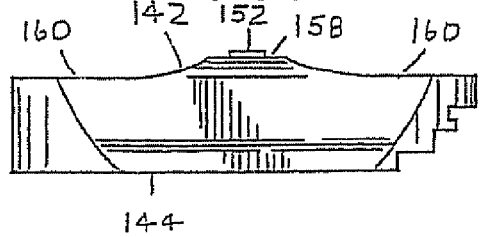

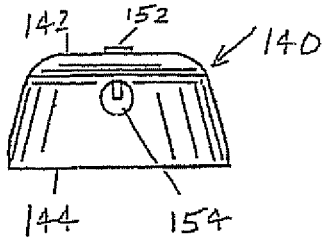
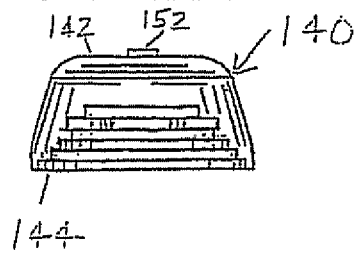
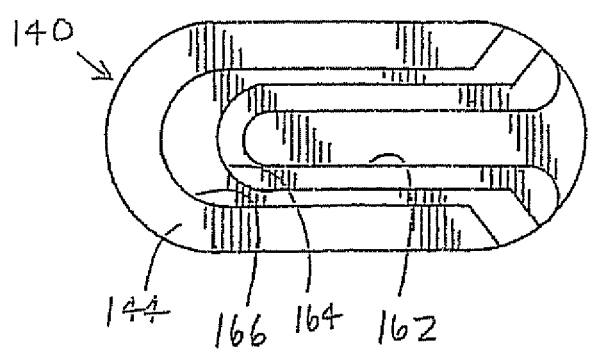
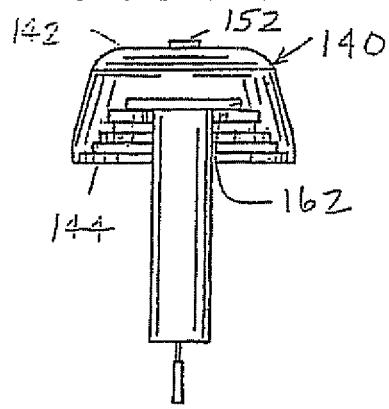
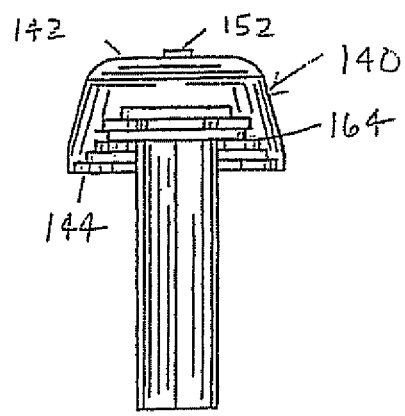
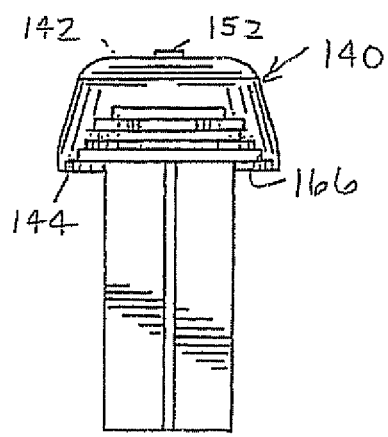

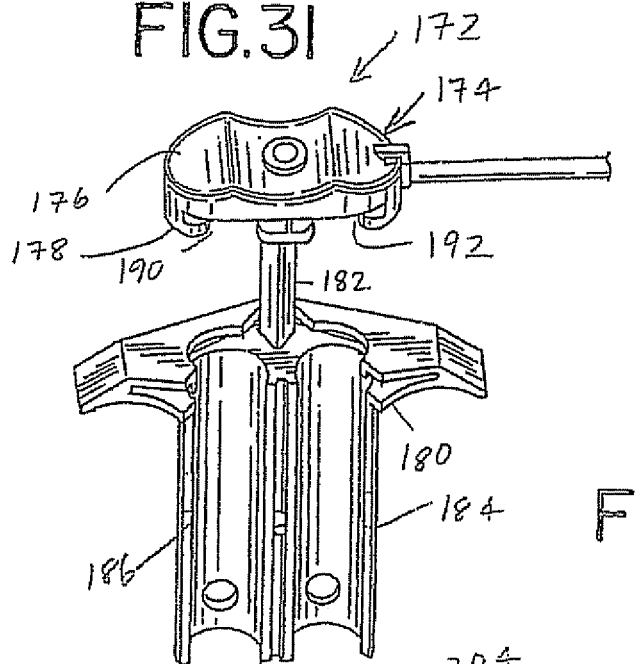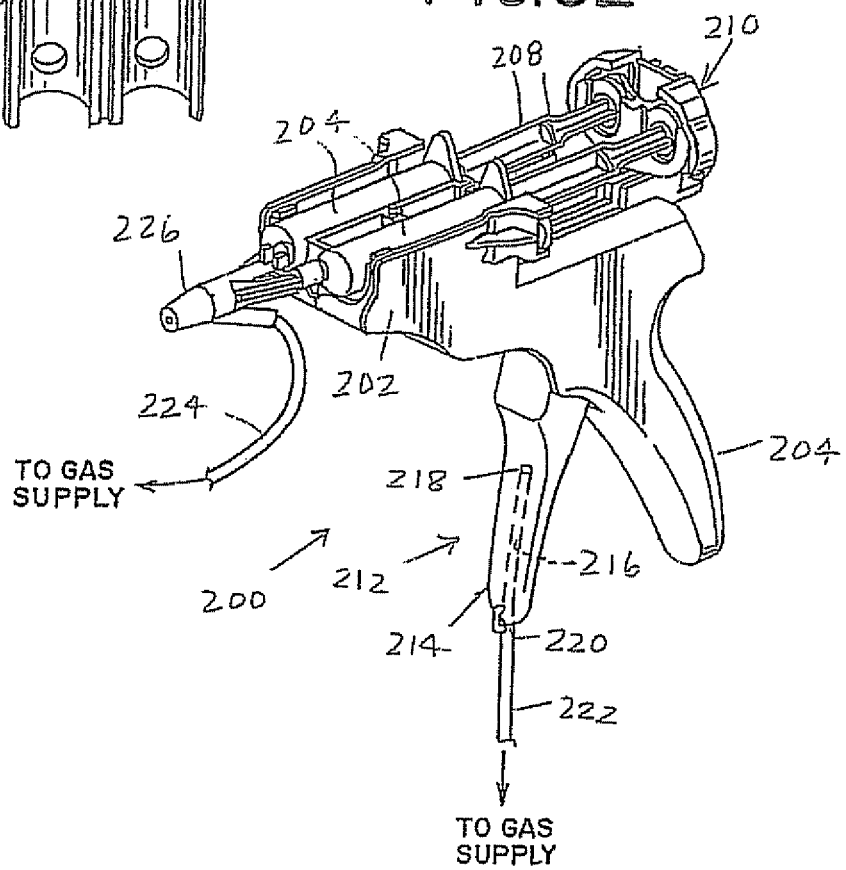

TISSUE SEALANT APPLICATOR SYSTEM

CROSS REFERENCE TO RELATED APPLICATION

This application is a continuation of U.S. patent application Ser. No. 12/390,014, filed Feb. 20, 2009, which is continuation of U.S. patent application Ser. No. 11/331,243, filed Jan. 12, 2006, now U.S. Pat. No. 7,537,174, which claims the benefit of U.S. Provisional Patent Application Ser. No. 60/643,368, filed Jan. 12, 2005, all of which are incorporated by reference in their entirety herein.

BACKGROUND

This invention relates to a system and apparatus for applying sealant, such as tissue sealant, to a work surface, such as biological tissue.

Mixing and/or applying sealant to work surfaces has application in a variety of settings. In the medical field, sealant in the form of tissue sealants have been applied to human and animal tissue, for example, to seal or repair tissue at a surgical or wound site, to stop bleeding, seal wounds, treat burns or skin grafts and a variety of other purposes.

In the medical field, tissue sealant has typically been applied by a syringe-type applicator that ejects tissue sealant directly onto the tissue. Examples of such applicators are shown in U.S. Pat. Nos. 4,846,405, 5,582,596, 5,665,067, 6,461,361 and 6,585,696, and PCT Publication No. WO 96/39212, all of which are incorporated herein by reference. Further examples of such applicators also are sold under the Tissomat and Duploject trademarks, which are marketed by Baxter AG.

The tissue sealant employed in treating biological tissue is typically made of one or more components, such as biocompatible compounds that can be absorbed by the body and do not require later removal from the patient. One example of a known tissue sealant is made of fibrinogen and thrombin. The tissue sealant may be contained in more than one container which can be mixed into an adhesive combination upon ejection from the tissue sealant applicator. For example, the components may exit from two separate outlets positioned in proximity with one another so that these components are mixed to create an adhesive tissue sealant upon ejection from the applicator.

Tissue sealant applicators also may provide tissue sealant that is atomized by means of pressurized, sterile gas such as, for example, air, to form a spray which is a combination of tissue sealant and a sterile gas or air. The applicator is connected to an air or gas source by tubing that supplies the gas or air to the distal end of the applicator in the vicinity of the outlets of the one or more tissue sealant components. For example, gas may communicate with one or more of the tissue sealant components within a mixing area defined by the applicator. Alternatively, the gas may mix with the tissue sealant components after ejection from the applicator. In the latter scheme, the gas or air outlet preferably is located in close proximity to the outlets of one or more of the tissue sealant components and may, for example, be in the form of an annular shaped outlet which surrounds at least one of the tissue sealant component outlets. The result is that the tissue sealant discharges in the form of an aerosol or spray.

The supply of gas or air is preferably coordinated so that, for example, gas is essentially simultaneously supplied to the applicator upon ejection of tissue sealant. However, synchronizing the timing of this supply with the ejection of tissue sealant or its components has proven awkward and difficult, particularly where multiple tissue sealant components are used.

Conventional tissue sealant applicators have relied on the user, such as a surgeon or hospital staff member, to simultaneously activate the supply of gas with the ejection of tissue sealant with separate motions. For example, the user is required to manually turn on and off the supply of gas, such as by foot actuation, in addition to the separate movement required to manually eject tissue sealant or components, such as, for example, by pressing on a syringe plunger or the like. It has proven difficult for the user to coordinate the timing of these two separate motions. Therefore, it is desired to provide a tissue sealant applicator which simplifies activation of a spray discharge of tissue sealant and which further provides a reliable and continuous spray discharge of tissue sealant.

SUMMARY OF THE INVENTION

The present invention is generally directed to a system and apparatus for applying or, an apparatus for use in applying, sealant, such as tissue sealant, to a work surface, such as biological tissue, in which a supply of gas may be reliably actuated essentially simultaneously with the ejection of the sealant and continue for a pre-determined time delay after the sealant has stopped ejecting.

In accordance with one aspect of the present invention, a tissue sealant applicator system includes a tissue sealant applicator having an elongate body forming a bore containing a tissue sealant component, a piston to eject the tissue sealant component from the bore, and a spray adaptor in fluid communication with the bore and forming a gas flow path. The system also includes a control unit adapted to be connected to a gas source, and a first gas passageway connecting the gas flow path and the control unit. The tissue sealant applicator further includes an actuating member cooperatively associated with the piston to eject the tissue sealant from the bore upon actuation by a user. The control unit is adapted to supply gas from the gas source to the first gas passageway essentially simultaneously with user actuation of the actuating member, and to permit the supply of gas to the spray adaptor from the gas source to continue to flow for a predetermined time delay after the user stops actuating the actuating member.

This summary is not intended as an exhaustive identification of each aspect or feature of the present invention that is now or may hereafter be claimed, but represents a summary of certain aspects of the present invention to assist in understanding the more detailed description that follows. Additional aspects or features of the present invention may be set forth in the following description.

Although described later in terms of certain structures, it should be understood that the system and apparatuses of the present invention are not limited to the identical structures shown. It should be understood that the structures described and claimed are intended to have a broad interpretation that includes all of the more specific structures, such as those mentioned above, in which it may find commercial application.

BRIEF DESCRIPTION OF THE DRAWINGS

FIG. 1 is a top perspective view of an apparatus, with portions of the apparatus being shown as transparent to aid illustration, and also includes a sealant applicator assembly, a control unit, and a gas supply source, shown schematically.

FIG. 2 is a back perspective view of the control unit shown in FIG. 1.

FIG. 3 is an enlarged top perspective view of the apparatus shown in FIG. 1.

FIG. 4 is a partial enlarged top perspective view of the proximal end of the apparatus shown in FIG. 1.

FIG. 5 is a bottom perspective view of the apparatus shown in FIG. 1.

FIG. 6 is a front perspective view of an actuating member of the apparatus.

FIG. 7 is a back perspective view of the actuating member.

FIG. 8 is a top view of the apparatus in FIG. 1.

FIG. 9 is a side view of the apparatus shown in FIG. 1.

FIG. 10 is a partial enlarged bottom view of the proximal end of the apparatus shown in FIG. 1.

FIG. 11 is a front view of a pusher member shown in FIG. 1.

FIG. 12 is a sectional view along line 12-12 of FIG. 11.

FIG. 13 is a rear view of the pusher member.

FIG. 14 is a pneumatic diagram of the control unit shown in FIG. 1.

FIG. 15 is a flow chart of an electrical circuit employed in the control unit.

FIG. 20 is a top perspective view of an alternative actuating member, with portions of the apparatus being shown removed to aid illustration.

FIG. 21 is a right side perspective view of the actuating member shown in FIG. 20.

FIG. 22 is a left side perspective view of the actuating member shown in FIG. 20.

FIG. 23 is a top view of the actuating member shown in FIG. 20.

FIG. 23A is a cross-sectional view taken along plane 23A shown in FIG. 23.

FIG. 24 is a rear view of the actuating member shown in FIG. 20.

FIG. 25 is a right side view of the actuating member shown in FIG. 20.

FIG. 26 is a left side view of the actuating member shown in FIG. 20.

FIG. 27 is a bottom view of the actuating member shown in FIG. 20.

FIG. 28 is a view similar to FIG. 26 further including a plunger member associated with the actuating member.

FIG. 29 is a view similar to FIG. 28 except that it includes a different plunger member having a larger diameter size than that shown FIG. 28.

FIG. 30 is a view similar to FIG. 29 except that it includes an alternate plunger member having a larger diameter size than shown in FIG. 29.

FIG. 31 is a top perspective view of an alternate embodiment of an apparatus of the present invention, with portions of the apparatus being shown removed to aid illustration.

FIG. 32 is a top perspective view of a yet further embodiment of an apparatus of the present invention.

DESCRIPTION OF THE PREFERRED EMBODIMENTS

Figure 16:
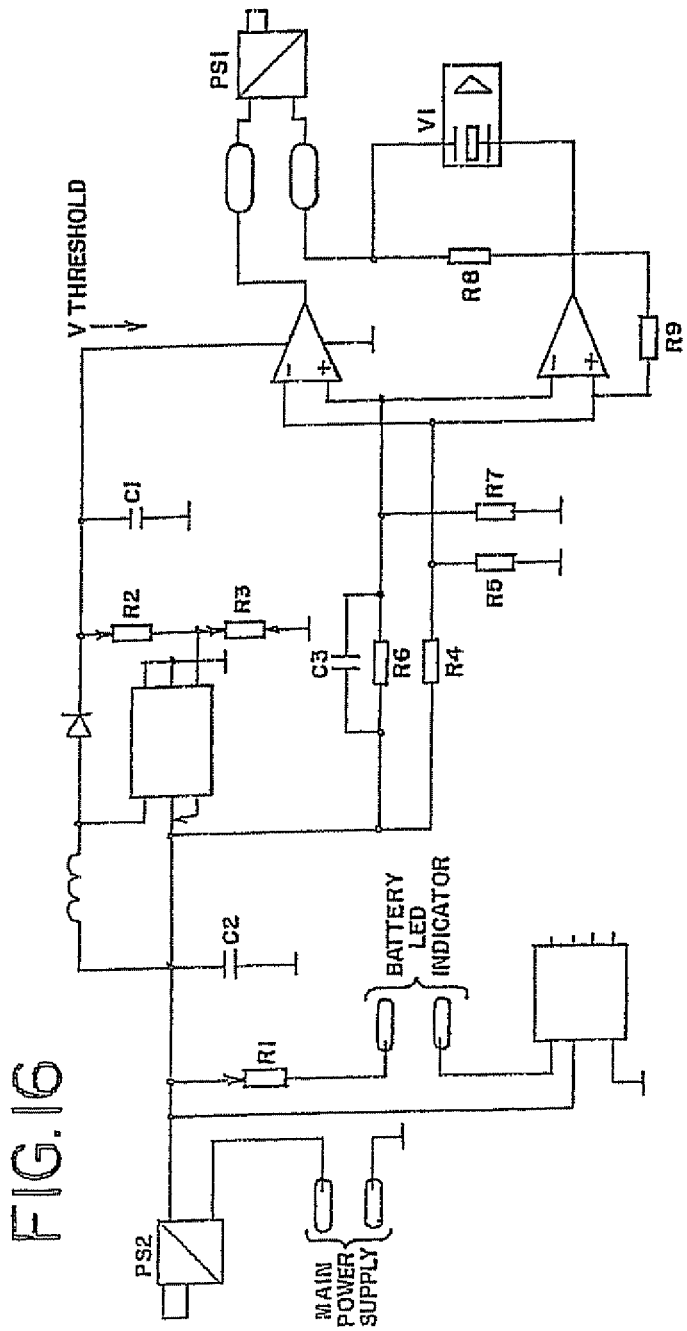
FIG. 16 is a schematic of an electrical circuit employed in the control unit.

In accordance with one aspect of the present invention, FIG. 1 generally illustrates a system for applying sealant, such as tissue sealant, to a work surface, such as biological tissue. The system preferably includes a tissue sealant apparatus, generally indicated at 2, a control unit, generally indicated at 4, and a pressurized, sterile gas or air supply source, generally indicated at 6. Each of these structures will be described in further detail below in accordance with various aspects of the invention.

In FIG. 1, the tissue sealant apparatus 2 includes a distal end, generally indicated at 12, and a proximal end, generally indicated at 14. The apparatus 2 is preferably connected to the control unit 4 by first and second gas passageways 8 and 10, respectively, which may be formed, at least in part, by tubing which preferably connects the control unit 4 and the apparatus 2. Generally, the first gas passageway 8 is associated or fluidly communicates with the distal end 12 of the apparatus and the second passageway 10 is associated with or fluidly communicates with the proximal end 14. Ends 15 of the tubing may have different shaped ends, such as male or female type connectors, where they are attached to the control unit 4 so as to allow for removable connection of the tubing to the control unit and prevent improper loading of the tubing on the control unit. The apparatus 2 is preferably constructed so that it may be easily disposed of after use.

The control unit 4 is preferably connected to the gas supply source 6 using a supply passageway 16 which extends from the control unit 4. It is also possible that the gas supply source 6 may be incorporated integrally with the control unit 4. The control unit 4 preferably supplies gas to one or both of the gas passageways 8 and 10, and which will be described in further below. The supply of gas may have a pressure range of approximately 3.5 to 7 bar, although other ranges are also possible. The control unit 4 further may include a pressure control knob 18 for manually controlling the pressure of gas supplied to the apparatus through at least one of the first and second gas passageways 8 and 10 and preferably the first gas passageway 8. A pressure gauge 20 may allow for visible monitoring of the pressure of the gas in the first gas passageway 8 to facilitate the setting of the desired pressure. In a preferred embodiment, the desired pressure ranges from 0.1 to 3 bar and the pressure gauge may indicate pressures from 0.0 to 4.0 bar.

As shown in FIG. 2, the rear surface of the control unit 4 may include a horizontally-disposed clamping member 22 and/or a vertical-disposed clamping member 24 having a biasing member 26 to assist attachment of the control unit to a table, rod, pole or other horizontally or vertically-disposed clamping surfaces during use.

In a further aspect of the present invention, the apparatus 2 of FIG. 1 generally includes an elongated body 28 having a proximal end, generally indicated at 27 and a distal end, generally indicated at 29. By way of example and not limitation, FIGS. 1 and 3 show the elongated body 28 defining two interior bores 30 and 32, for example, an apparatus of the type having a double-barrel syringe applicator where each barrel contains a tissue sealant component. Each bore 30 and 32 is adapted to contain a component of the tissue sealant. For example, each bore may contain one of fibrinogen or thrombin or other like tissue sealant components. The illustrated structure is shown by way of example and not limitation and it is realized that other structures are also possible. For example, the apparatus may employ alternative structures, such as single and multiple interior bores, and such structure may depend on the type of sealant employed.

As shown in FIG. 3, a frame 34 preferably carries the interior bores 30 and 32 within a corresponding cavity 36 and 38 so that the interior bores extend along an axis parallel to each other. The frame 34 may also define slots 40 and 42, shown in FIG. 3, at a proximal end of the frame in which a flanged end 44 and 46 of the corresponding bore 30 and 32 is received. A piston 48 and 50 is movably positioned in each respective interior bore 30 and 32.

A pusher member, generally indicated at 52, is operatively associated with the pistons 48 and 50 and includes plunger members 53 and 54 that extend through the proximal end of each bore 30 and 32 corresponding to each piston 48 and 50. Movement of the pusher member 52 toward the distal end 12 of the apparatus 2 simultaneously moves the pistons 48 and 50 to eject the tissue sealant contained therein. As shown in FIGS. 8 and 9, an extension arm 56 may be provided which extends proximally from the frame 34 parallel to the plunger members 52 and 53 to a proximal platform 58 of the pusher member 52 and is slidably attached to the frame to allow for movement of the pusher member 52 relative to the body 2. In FIGS. 3-4, a flanged end 60 and 62 of each respective plunger member 53 and 54 may be received in a corresponding slot 64 and 66 (also shown in FIGS. 12-13) defined in a distal surface 68 of the proximal platform 58, so as to synchronize the movement of the plunger members 53 and 54 by pressing on the pusher member 52. In an alternate embodiment, the pusher member 52 may be comprised of integrally attaching the plunger members 53 and 54 with proximal platform 58.

As shown in FIGS. 10-12, the pusher member 52 is provided with a proximal surface 70 which includes two ridges 72 spaced from one another extending from a bottom edge 76 to a top edge 78 of the pusher member 52. As shown in FIGS. 11 and 12, a ramp 74 is preferably positioned on each ridge 72 and is spaced between the top and bottom edges 76 and 78. In FIG. 12, the ramp 74 forms an inclined surface which extends from a recessed edge 79 defined near the bottom edge 76 to a notch 80 defined near the top edge 78. Preferably, each ramp 74 is inclined at a 2° angle from the recessed edge 79 to the notch 80. As shown in FIGS. 10 and 11, two channels, grooves or the like 82 and 84 are preferably formed in the proximal surface 70 in the valley defined between the ridges 72. The channels 82 and 84 extend into the proximal surface 70 in a distal direction at an oblique angle, as best shown in FIG. 10.

Turning to FIGS. 4-5, an actuating member, generally indicated at 86, is cooperatively associated with the pistons 48 and 50 to eject sealant. By "cooperatively associated" it is meant that the actuating member may be part of the structure that actuates the ejection the sealant or the actuating member may be operatively attached to or carried by such structure or may be separate from the structure but interactive directly or indirectly with such structure. In FIGS. 4-5, the actuating member is preferably removably carried by or mounted to the pusher member 52. It is also possible for the actuating member to be formed integrally with the pusher members (as shown in FIGS. 22-31) and/or with other elements of the apparatus (as shown in FIG. 32). In FIGS. 4-5, the actuating member is connected to the proximal end of the pusher member 52 although other locations are also possible.

The actuating member is also operative to actuate a supply of gas to create a spray discharge, simultaneously with the ejection of tissue sealant. It is contemplated that the actuating member may be operable to actuate a spray discharge in a variety of ways. Actuation by the actuating member may be provided by air, pressure, electricity and other mechanisms. By way of example and not limitation, it is possible that the actuating member may be operated for actuation by an electrical switch or the like. Actuation may also be triggered by a variation in a control gas pressure, either by an increase or decrease. This description is not exhaustive of the techniques which may be employed to create actuation of a spray discharge and it is realized that other variations are possible in addition to those discussed herein.

Preferably, the actuating member comprises a second gas passageway that includes an opening which permits gas flow. The second gas passageway may be placed in fluid communication with the supply signal input of the gas supply device. Upon user actuation of the actuation member to move the piston, the opening is restricted, generating the supply signal to the gas supplying device. In FIG. 6, the actuating member 86 preferably includes a proximal portion 88 which defines a user-contact surface and a distal portion 90 which attaches to the pusher member 52. Although the user-contact surface will be described by specific structures below, these are shown by way of example and not limitation. It is contemplated that the user-contact surface may be associated with a manually or electrically-actuated switch which causes a variation in gas or pressure or generates an electrical signal so as to actuate the supply of gas to the first gas passageway 8. It is also possible that the user-contact surface may be associated with different portions of the actuating member 86 other than the proximal portion 88.

In FIGS. 6-7, the proximal portion 88 preferably includes a depression 92 having a concave shape or configuration that is adapted to receive a user's finger, such as a thumb. The depression 92 may include a tubular protrusion 94 positioned in the depression 92 such that the user's finger generally contacts this protrusion 94 during ejection of tissue sealant. In FIG. 6, the protrusion 94 is preferably defined around an opening 96. As shown in FIG. 5, the actuating member 86 preferably forms a portion of the second flow passageway 10 and the opening 96 permits gas flow to or from the second gas flow passageway 10. Upon user actuation of the actuation member to move the piston, the opening is restricted, generating the supply signal to the gas supplying device. In FIG. 5, tubing which preferably defines another portion of the second flow passageway 10 fluidly communicates with the actuating member 86 by connection to a flow port 102 defined in the actuating member on one side thereof, as shown in FIG. 6. Although the positioning of the opening 96 and the flow port 102 are shown in FIGS. 5-7 on the proximal portion 88 and a side portion, respectively, of the actuating member 86, other variations are also possible.

As shown in FIG. 7, the actuating member 86 preferably defines two parallel ribs 98 and 99 extending from the distal portion 90. The ribs 98 and 99 may extend between the side edges 97 and preferably are generally symmetrical about a lateral line A. The actuating member 86 also preferably includes two angled projections 100 and 101 which are positioned between the ridges 98 and 99 and extend in a distal direction at an oblique angle. The projections 100 and 101 generally are symmetrical about a vertical line B. As shown in FIG. 10, each projection 100 and 101 is preferably shaped and angled to be received by the corresponding channels 82 and 84 such that the actuating member 86 is removably attached to the pusher member 52. Other fastening structures may be employed to connect the actuating member other than the structures shown and described. Further, attachment may be provided by a projection formed in the pusher member 52 which is received by the actuating member 86.

As shown in FIG. 10, the actuating member may be removably attached by slidably inserting the projections 100 and 101 into the corresponding channels 82 and 84. With reference also to FIG. 11, during insertion, the ribs 98 and 99 traverse the ridges 72 and ramps 74 until the leading rib 98 is received by the notches 80 and the following rib 99 engages the recessed edge 79. The projections 100 and 101 engage channels 82 and 84. The inclined surfaces of the ramps 74 preferably contact the leading rib 98 causing the actuating member to slightly flex in a leaf spring-like manner and provide increased resistance to movement as the incline increases. Such that, when the rib 98 slides past the ramps 74 and engages the notches 80 and rib 99 slides over the ridge 72 and engages the recessed edge 79, the user feels less resistance and, more preferably, feels a tactile sensation and possibly an aural indication. The actuating member 86 may be slidably removed by the user urging the rib 98 out of notch 80 and along the ramps 74 and moving the rib 99 out of the recessed edge 79. The ribs 98 and 99 preferably have sufficient flexibility to permit slidable insertion and removal. It is also possible to attach the actuating member to the pusher member 52 in an orientation 180 degrees rotated relative to orientation shown in the drawings, for example, where it is desired that the tubing may extend from the other side of the actuating member.

Figure 19:
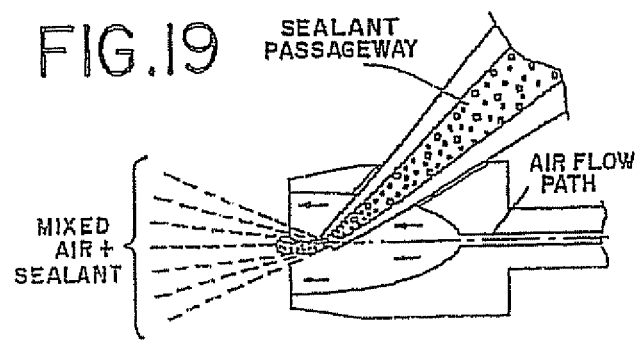
FIG. 19 shows yet another modified spray adaptor in which gas mixes with both of the sealant components after the components are mixed together.

Turning to FIGS. 8 and 9, a spray adaptor 104 is provided that is preferably carried by or connected to the distal end 29 of the body. In FIG. 8, distal outlets 106 and 108 may be associated with the respective interior bores 30 and 32 of the body 28 to allow ejection of the sealant components and for communication with the spray adaptor 104. Respective sealant passageways 110 and 112 may be formed in the spray adaptor 104 to communication of sealant from the respective interior bores 30 and 32. The spray adaptor 104 may define separate outlets 114 and 116 for each sealant component, as shown in FIG. 8, or, alternatively, may allow ejection of a mixed component stream, as shown in FIG. 19, in which the mixture of the components is provided inside the spray adaptor 104. It is contemplated that the spray adaptor 104 in FIGS. 8 and 9 shown by way of example and not limitation, and other configurations are possible.

Figure 17:
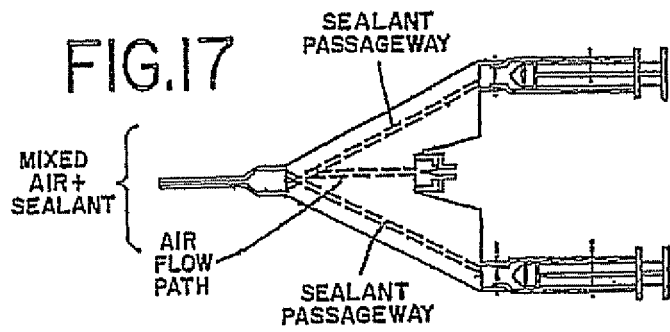
FIG. 17 shows a modified spray adaptor in which gas mixes with one of the sealant components.
Figure 18:
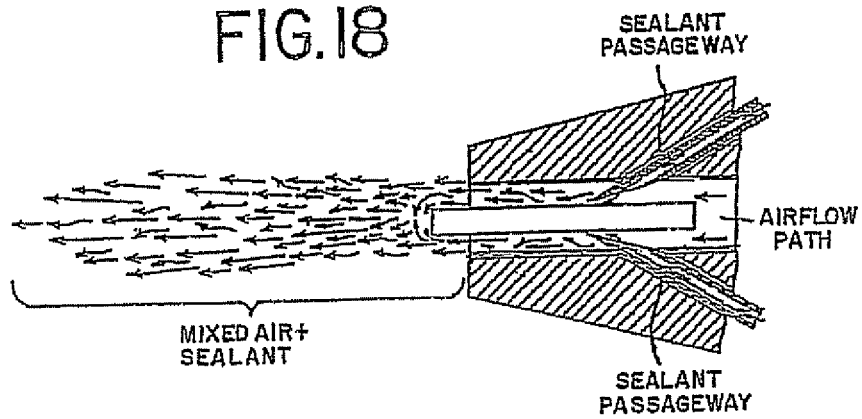
FIG. 18 shows another modified spray adaptor in which gas separately mixes with each of the sealant components.

In FIG. 9, the spray adaptor 104 also preferably forms a portion of the first gas passageway 8 and preferably connects to the tubing that forms another portion of the first gas passageway 8. In FIGS. 8 and 9, the spray adaptor 104 defines a gas flow path 118 which communicates with a gas outlet 120. In FIGS. 8 and 9, a portion of the gas flow path 118 preferably has an annular or circular shape, although other shapes are also possible, such as, for example, oval, oblong, or the like. FIGS. 8 and 9 also show the gas outlet 120 disposed around the sealant outlets 114 and 116 although other variations are also possible including where a separate gas outlet is disposed around each sealant outlet. It is possible for the gas to mix with at least one of the sealant components either before or after the components are mixed together. In FIGS. 17-18, gas mixes with one of the sealants, as in FIG. 17, and or two sealants, as in FIG. 18, before the sealant components are mixed together and, in FIG. 19, gas mixes with an already mixed sealant upstream of a combined gas and sealant distal outlet. The operation of the actuating member 86 preferably provides a supply of gas to the spray adaptor 104 through the first gas passageway 8 simultaneously with the ejection of sealant.

In accordance with another aspect of the present invention, a sealant applicator assembly 122, as best shown in FIG. 1, is provided that includes a spray adaptor 104, a first gas passageway 8 and an actuating member 86, as shown and described above. These structures of the sealant applicator assembly preferably are attached to one another in the configuration shown in FIG. 1, and may be sold as a disposable set for use with a double-barrel syringe plunger structure for ejecting tissue sealant, similar to the syringe plunger structure shown and described above, or other like structures. The spray adaptor and actuating member of the sealant applicator assembly are preferably removably attached to the appropriate locations of the syringe plunger structure, similar to the above description. By way of example and not limitation, the syringe plunger structure may be used and adapted for use with other sealant applicator assembly disposable sets which contain other adaptors, such as a catheter or cannula, or other adaptors for that provide a spray or non-spray discharge of tissue sealant. It is also possible for the syringe plunger structure to be included with the sealant applicator assembly as a combined disposable set.

In accordance with a yet further aspect of the present invention, the control unit 4 may be provided for use with any of the described system and apparatuses. As shown in FIG. 1, the control unit 4 is cooperatively associated with the apparatus to simultaneously activate the supply of gas with the ejection of tissue sealant. By way of example and not limitation, FIGS. 14-16 show an example of the control unit 4 which may be used to supply and control gas to the first and second gas passageways 8 and 10. It is contemplated that this description is not exhaustive and that modifications to the control unit 4 are possible and will depend on the structures employed to apply tissue sealant and how they are operated or actuated, such as for example, by pneumatic, electric, or other types of actuation techniques.

As shown in FIG. 14, the control unit 4 may be supplied by gas from the gas supply source 6 through a supply passageway 16. The incoming gas supply may be filtered by a filter IF1. The supply of gas may flow to a first flow branch 126 and a second flow branch 128. Each flow branch 126 and 128 preferably includes a corresponding pressure regulator PR1 and PR2. Each pressure regulator preferably is configured to monitor the pressure along its respective flow branch and may further be adjustable to accommodate variations in tubing, such as the inner diameter and length of such tubing.

In the first flow branch 126, the pressure of gas preferably is adapted for manual control and/or adjustment by the user by way of the pressure control knob 18, as shown in FIG. 1. In FIG. 14, a pressure gauge PG1, as also shown at 20 in FIG. 1, and a flow controller FC2 may also be provided to monitor the pressure, which preferably may be in the range of approximately 0 to 3 bars, and more preferably may be in the range of approximately 2 to 3 bars. In FIG. 14, the first flow branch 126 preferably includes an outlet 127 which is adapted for communication with the first flow passageway 8 so as to control the desired spray discharge pressure and further includes a pressure safety switch PS1 and a supply valve V1. The supply valve V1 may be normally biased to a closed position such that no gas is supplied to the first gas passageway 8 and, thus, no spray discharge is created. The pressure safety switch PS1 and supply valve V1 will be described in further detail below.

In FIG. 14, the second flow branch 128 may include a corresponding flow controller FC1 and preferably maintains a control gas pressure. The control gas pressure is preferably a predetermined pressure or pressure range, which may be set during the manufacturing process. The control gas pressure preferably is in the range of approximately 0.01-0.20 bar, and more preferably in the range of approximately 0.05-0.15 bar. With reference to FIGS. 4-5, the control gas pressure is preferably supplied through an outlet 129 (FIG. 14) to the second gas passageway 10 to exit the opening 96 defined in the actuating member 86. The control gas pressure is preferably sufficient to provide a tactile sensation to the user's finger so as to indicate to the user when such finger is positioned over the opening 96. Alternatively, it is also possible for the control gas pressure to be maintained under conditions such that gas does not exit the opening 96.

As shown in FIG. 14, the control unit 4 further preferably comprises a pressure switch PS2 which communicates with the flow branch 128. The pressure switch PS2 is preferably operably associated with the supply valve V1 which communicates with the other flow branch 126. The pressure switch PS2 is operable to open the supply valve V1 such that gas is supplied to the first gas passageway 8 thus providing a spray discharge of tissue sealant. The pressure switch PS2 preferably activates to open the valve in response to receiving a control signal from the apparatus. The control signal is created when the user-applied force is supplied to eject tissue sealant.

The user-applied force simultaneously causes a variation in pressure. Such user-applied force preferably restricts or occludes the exit of gas from the opening 96 so as to prevent gas from exiting the opening and cause an increase in pressure sufficient for the control signal to be received by the pressure switch. Alternatively, in an alternate embodiment, it is possible that the user-applied force may trigger a decrease in pressure if the user-applied force allows gas to be released from the opening which otherwise does not exit the opening 96. The pressure switch PS2 preferably monitors for such variation in pressure in the second gas passageway 10 and activates to open or close the valve in response to such variation in pressure. The resulting spray discharge provides a combined gas and tissue sealant spray from the distal end of the apparatus 2. When the user-applied force is removed, the ejection of tissue sealant may stop immediately, or, alternatively, the supply of gas may be stopped after a predetermined time delay.

As shown in FIG. 14, a timing delay control member PFC1 may be operatively connected to the control unit 4, such as the pressure switch PS2. The timing delay control member PFC1 preferably prevents the pressure switch PS2 from closing the valve for a predetermined period of time after the user applied force is removed. In FIG. 14, the timing delay control member PFC1 preferably communicates with the flow passageway 118 (shown in FIGS. 8-9) and may utilize additional tubing 130. Preferably, the time delay is within the range of approximately 0.1 seconds to 0.9 seconds and, more preferably, approximately 0.5 seconds. The time delay provides a discharge of gas after the user has stopped the ejection of tissue sealant. The additional gas discharge may be helpful in dislodging any remaining tissue sealant from the distal end of the apparatus so as to prevent clogging or fouling of the distal end.

As further shown in FIG. 14, a pressure safety switch PS1 may communicate with the flow passageway 126 and provided for overpressure protection. The pressure safety switch preferably prevents the pressure of the supply of gas to the apparatus from exceeding a predetermined threshold level. When the threshold level is reached, the supply of gas to the distal end of the apparatus may be automatically shut off.

FIGS. 15 and 16 illustrate a flow chart and schematic of an electrical circuit which may be used in connection with the operation of the pressure switch PS2 and the supply valve V1, as described above. As shown in FIG. 16, the pressure switch PS2 is connected to a main power supply, such as a battery. A battery LED indicator may be used to indicate when the battery is running out of the necessary charge. As shown in FIGS. 15 and 16, the activation of the pressure switch PS2 closes the electronic circuit so as to supply voltage to the valve V1, thus, opening the valve V1. In FIG. 16, the voltage which is supplied to the valve V1 is compared to a predetermined threshold voltage $V_{THRESHOLD}$. If the voltage exceeds the threshold voltage $V_{THRESHOLD}$, then the pressure safety switch PS1 overrides the pressure switch PS2 and closes the valve V1.

The pusher member may be integral with the actuating member. Alternatively, the pusher member may be separate from and adapted to be cooperatively associated with the actuating member. An alternative embodiment of an actuating member, generally indicated at 140, is shown in FIGS. 20-30 for use with an apparatus similar to the apparatus described in FIGS. 1-16. Such embodiment is similar to the embodiment described in FIGS. 6-7, except that the embodiment in FIGS. 20-30 includes an actuating member 140 which is formed as an integral part of the pusher member or members that are associated with a conventional syringe piston construction. Accordingly, those portions of the apparatus which are identical to those portions in FIGS. 1-16 will not be repeated.

In FIGS. 20-30, the actuating member 140 includes a proximal or top portion 142 which defines a user-contact surface and a distal portion or underside 144 which attaches to plunger members 146 and 148 of the syringe(s). In FIG. 23A, the actuating member 140 may define a gas passageway 150 which extends between first and second ends 152 and 154. The first end 152 may be defined in the user contact surface 142 (as shown in FIGS. 20-24) and the second end 154 of the passageway 150 may be defined along a side edge of the actuating member extending between the proximal and distal portions 142 and 144 (or top side and underside, respectively) (see FIGS. 21, 23A and 25 or elsewhere that is convenient). With reference to FIG. 20, the second end 154 of the passageway 150 preferably communicates via tubing 156 to a control unit and gas or pressure source (such as indicated at 4 and 6 in FIG. 1).

In FIGS. 20-24, the proximal portion or user-contact surface 142 has a contoured surface different than that shown in FIGS. 1-13. Although other contours are also possible, and the present application is not limited to the contoured surfaces shown herein, the proximal portion 142 in FIGS. 20-24 preferably includes a raised central portion 158 in which the first end 152 of the passageway 150 may be defined and concave portions 160 which extend to each side of the raised portion 158. As shown in FIG. 24, the first end 152 of the passageway 150 may terminate slightly above the raised portion 158 so that the user may determine the location of the first end 152 based on tactile feel. Alternatively, for example, the first end 152 may be recessed or flush with the raised portion 158.

As shown in FIGS. 22, 23A and 26-30, the distal portion or underside 144 includes laterally disposed slots 162, 164 and 166 for receiving plunger members 146 and 148 having differently sized flanged ends. As best seen in FIGS. 28-30, small, medium and large diameter-sized flanged ends may be received in correspondingly-sized slots 162, 164 and 166. The size of the flange is typically different for different size (volume) syringes. This allows one actuator to accommodate different syringe sizes (volumes) that may be needed for different procedures. As shown in FIG. 27, each of the slots 162, 164 and 166 may be sized and configured to receive a single plunger member or a pair of plunger members oriented in a side-by-side relationship.

In accordance with the above described invention, the embodiment of FIGS. 20-30, may be associated with the control unit 4 (as shown in FIG. 1) to supply and control gas from a gas source. In FIGS. 20-30 the gas passageway 150 is occluded by the user when the user's thumb is placed over the second opening 152 formed in the user-contact surface 142. In accordance with previously described embodiments, the gas passageway 150 may fluidly communicate with the control unit and/or gas or pressure source (e.g., indicated at 4 and 6 in FIG. 1) via tubing 156 connected to the second end 154 of the gas passageway 150. In FIG. 20, such connection may be achieved by attaching an end of the tubing 156 having a projection or hook 168 which engages a behind a ramped detent or lug 170 on the user contact surface 142. Other types of fastening structures are also possible and are not limited to those shown and described. In accordance with the invention described above, when the second opening 152 is occluded by the user, a supply of gas is preferably supplied to the distal end of the applicator via appropriate tubing (e.g. as indicated at 8 in FIG. 1).

In FIG. 31, an apparatus, indicated generally at 172, includes an actuating member 174 which is also combined with the pusher member, similar to the previously described embodiments, and includes a top side or user-contact surface 176 having a contour similar to that shown in FIGS. 1-13 and a distal or underside portion 178. Similar to the embodiment shown in FIGS. 1-13, the embodiment in FIG. 31 includes a frame 180 having a slidable extension arm 182 and includes a pair of adjacent hollow cavities 184 and 186. The cavities 184 and 186 receive respective cylindrical bores (not shown) containing tissue sealant components. The distal portion (or underside) 178 of the actuating member 172 preferably includes two slots 190 and 192 which each slidably receives a flanged end of a plunger member extending proximally from each fluid-containing bore disposed in respective cavities 184 and 186.

FIG. 32 shows an alternate tissue sealant apparatus, indicated generally at 200. Such apparatus is shown having a conventional gun-type applicator construction, although other constructions are also possible. The apparatus 200 generally defines a body 202 and a handle 204. The body 202 defines respective cavities for receiving fluid-filled cylindrical bores 206 having respective plunger members 208 extending therefrom. Each proximal end of the plunger member 208 is received by a pusher member 210. An actuating member, generally indicated at 212, is preferably operatively associated with the pusher member 210. The actuating member 212 includes a lever 214 which may be distally located and pivotally movable relative to the handle 204. The lever 214 may be operatively connected to the pusher member 210 by a drive mechanism shown and described in U.S. Pat. No. 6,585,696, which is assigned to Baxter International Inc., the assignee of the present application, and which patent is incorporated herein by reference. Accordingly, such mechanism need not be described further.

In FIG. 32, the lever 214 is preferably pivotally connected to the handle 204. The lever 214 may be pivoted in a direction towards and/or away from the handle 204 for actuation. The lever 214 also preferably defines at least a portion of a gas passageway 216. A first end or opening 218 of the passageway 216 is preferably defined in a distal portion of the lever 214. To activate the supply of tissue sealant, the user may cover or occlude the first end 218 of the passageway 216, such as with an index finger. A second end 220 of the passageway 216 preferably connects to a supply of gas via tubing 222 which preferably defines another portion of the gas passageway 216 so as to provide gas or pressure to the passageway 216. A supply of gas is also preferably supplied to the distal end of the apparatus 200 via appropriate tubing 224.

During operation of the apparatus 200 in FIG. 32, the lever 214 pivotally moves to eject tissue sealant from the bores 206 through the spray end 226 of the device. Gas or pressure may be simultaneously supplied to the spray end 226 through tubing 224 upon occlusion of the opening 218 formed in the lever 214, in accordance with the above described invention. The supply of gas may be stopped, either immediately or with a time delay, when the user stops occluding the opening 218, also in accordance with the above described invention.

As can be seen from the above description, the present invention has several different aspects, which are not limited to the specific structures shown in the attached drawings. Variations of these structures may be embodied in other structures for carrying out application of tissue sealant.

The invention claimed is:

1. A tissue sealant applicator system comprising:
   a tissue sealant applicator including an elongate body forming a bore containing a tissue sealant component, a piston to eject the tissue sealant component from the bore, and a spray adaptor in fluid communication with the bore and forming a gas flow path;
   a control unit adapted to be connected to a gas source and disposed in a housing separate from the tissue sealant applicator; and
   a first gas passageway connecting the gas flow path and the control unit;
   the tissue sealant applicator further including an actuating member cooperatively associated with the piston to eject the tissue sealant from the bore upon actuation by a user, and
   the control unit adapted to supply gas from the gas source to the first gas passageway essentially simultaneously with user actuation of the actuating member, and to permit the supply of gas to the spray adaptor from the gas source to continue to flow for a predetermined time delay after the user stops actuating the actuating member.

2. The system according to claim 1, wherein the control unit comprises a pressure switch connected to the actuating member and a valve connected between the spray adapter and the gas source, the valve having an open state and a closed state and activation of the pressure switch causing the valve to move from the closed state to the open state.

3. The system according to claim 2, further comprising a timing delay control member operatively connected to the pressure switch and adapted to prevent deactivation of the pressure switch from causing the valve to move to the closed state for the predetermined time delay after the user stops actuating the actuating member.

4. The system according to claim 3, wherein the timing delay control member comprises a check valve and a flow controller connected in parallel.

5. The system according to claim 1, wherein the actuating member comprises a user-contact surface associated with a pressure switch that causes a variation in pressure or generates an electrical signal to cause the control unit to supply gas from the gas source to the first gas passageway.

6. The system according to claim 5, further comprising a second gas passageway connected between the gas source and the actuating member to create a flow path therebetween, the pressure switch in communication with the flow path.

7. The system according to claim 6, wherein the second gas passageway includes an opening, the opening disposed on the user-contact surface.

8. The system according to claim 7, wherein a proximal portion of the actuating member includes a depression having a concave shape to receive a user's finger, the depression including a protrusion defined around the opening.

9. The system according to claim 1, wherein:
   the control unit comprises a first flow branch adapted to be connected to the gas source, and a second flow branch connected to the gas source and the actuating member,
   the control unit being adapted to control the first flow branch to supply gas to the spray adaptor from the gas source essentially simultaneous with a force applied to the actuating member, and to control the second flow branch to permit the flow of gas to the spray adaptor from the gas source for a predetermined time delay after the user stops actuating the actuating member.

10. The system according to claim 9, further comprising a pressure switch in communication with the second flow branch and a valve disposed in the first flow branch, the valve having an open state and a closed state and activation of the pressure switch causing the valve to move from the closed state to the open state.

11. The system according to claim 10, further comprising a timing delay control member disposed between the pressure switch and the second flow branch and adapted to prevent deactivation of the pressure switch from causing the valve to move to the closed state for the predetermined time delay after the user stops actuating the actuating member.

12. The system according to claim 11, wherein the timing delay control member comprises a check valve and a flow controller connected in parallel.

13. The system according to claim 12, wherein the control unit has a single inlet adapted to be connected to a gas source, the first and second flow branches connected to the single inlet and each of the first and second flow branches having a flow controller to maintain a gas pressure in the first or second flow branch.

14. The system according to claim 1, wherein the gas source comprises a source of pressurized, sterile gas or air.

15. The system of claim 1 further comprising:
a plunger member connected to the piston with a distal end disposed within the bore and a proximal end depending from the bore,
the actuating member carried by the proximal end of the plunger member to move with plunger member as plunger member moves along the bore and adapted to cause sealant component to be ejected from the bore and gas to be supplied essentially simultaneously with ejection of the sealant component from the bore when force is applied to the actuating member, and
the bore communicating through one or more outlets with the spray adaptor to allow ejection of the tissue sealant component.

16. The system according to claim 15, further comprising:
another bore containing a tissue sealant component;
an another piston to eject the tissue sealant component from the another bore; and
an another plunger member connected to the another piston with a distal end disposed in the another bore and a proximal end depending from the bore,
the actuating member carried by the proximal end of the another plunger member to move with the another plunger member as the another plunger member moves along the another bore, and
the another bore communicating through one or more outlets with the spray adaptor to allow ejection of the tissue sealant component.

17. The system according to claim 16, wherein the applicator comprises a platform connected to the proximal ends of the plunger member and the another plunger member, the actuating member mounted to the platform to be carried on the proximal ends of the plunger member and the another plunger member.

18. The system according to claim 17, wherein the actuating member is removably carried by the platform.

19. The system according to claim 17, wherein the actuating member is formed integrally with the platform.

20. The system according to claim 17, wherein the applicator comprises a frame that carries the bore and the another bore, and an extension arm slidably attached to the frame at a distal end and connected to the platform at a proximal end.

21. The system according to claim 1, wherein the first gas passageway is defined by disposable tubing connected at a first end to the control unit and a second end to the gas flow path, the disposable tubing being removably connectable to the control unit.

22. The system according to claim 1, wherein the tissue sealant applicator and the first gas passageway are disposable, and the control unit is not disposable.

23. The system according to claim 1, wherein the control unit comprises a clamping member to assist attachment of the control unit to a clamping surface.

* * * * *